United States Patent [19]

Bøgesø et al.

[11] Patent Number: 5,643,784
[45] Date of Patent: Jul. 1, 1997

[54] INDAN DERIVATIVES

[75] Inventors: Klaus P. Bøgesø, Lyngby; Peter Bregnedal, Allerød, both of Denmark

[73] Assignee: H, Lundbeck A/S, Copenhagen-Valby, Denmark

[21] Appl. No.: 383,708

[22] Filed: Feb. 1, 1995

Related U.S. Application Data

[63] Continuation of Ser. No. 105,187, filed as PCT/DK91/00358, Nov. 28, 1991, abandoned.

[30] Foreign Application Priority Data

Dec. 4, 1990 [DK] Denmark ................. 2869/90

[51] Int. Cl.$^6$ ............... A61K 31/495; A61K 31/505; C07D 403/06; C07D 413/06
[52] U.S. Cl. ............ 514/228.8; 514/252; 514/253; 514/255; 544/96; 544/285; 544/286; 544/295; 544/366; 544/367; 544/368; 544/369; 544/370; 549/77; 549/78; 558/426; 568/327; 568/808
[58] Field of Search ................ 544/285, 286, 544/295, 366, 370, 399, 400, 367, 403, 369, 368, 372, 373, 96; 514/252, 253, 255, 228.8

[56] References Cited

U.S. PATENT DOCUMENTS

| | | | |
|---|---|---|---|
| 2,891,066 | 6/1959 | Parcell | 260/294.3 |
| 3,135,794 | 6/1964 | Archer | 260/562 |
| 3,408,356 | 10/1968 | Horovitz | 260/294.3 |
| 3,476,760 | 11/1969 | Kaiser et al. | 546/201 |
| 3,558,637 | 1/1971 | Kaiser et al. | 546/201 |
| 3,980,658 | 9/1976 | Possanza et al. | 260/293.61 |
| 3,993,764 | 11/1976 | Dumont et al. | 424/267 |
| 3,996,211 | 12/1976 | Lassen | 260/240 |
| 4,038,395 | 7/1977 | Lassen | 424/250 |
| 4,139,634 | 2/1979 | Pigerol et al. | 424/274 |
| 4,196,209 | 4/1980 | Dumont et al. | 424/267 |
| 4,208,417 | 6/1980 | Uzan et al. | 424/267 |
| 4,251,538 | 2/1981 | Hausberg et al. | 424/267 |
| 4,333,939 | 6/1982 | Guillaume et al. | 424/263 |
| 4,358,456 | 11/1982 | Ward | 424/267 |
| 4,443,448 | 4/1984 | Bogeso | 544/398 |
| 4,525,360 | 6/1985 | Perregaard | 514/277 |
| 4,530,932 | 7/1985 | Clemence et al. | 514/318 |
| 4,670,447 | 6/1987 | Strupczewski | 514/322 |
| 4,684,650 | 8/1987 | Bogeso | 544/367 |
| 4,701,462 | 10/1987 | Wyllie | 514/323 |
| 4,710,500 | 12/1987 | Perregaard | 514/254 |
| 4,772,612 | 9/1988 | Goldmann et al. | 514/302 |
| 4,831,031 | 5/1989 | Lowe, III et al. | 514/254 |
| 4,847,254 | 7/1989 | Boegesoe et al. | 514/256 |
| 4,853,470 | 8/1989 | Strupczewski | 546/199 |
| 4,873,344 | 10/1989 | Bogeso et al. | 541/77 |
| 4,946,863 | 8/1990 | Boegesoe et al. | 514/447 |
| 4,997,841 | 3/1991 | Oxford et al. | 514/323 |
| 5,036,078 | 7/1991 | Coates | 514/323 |
| 5,068,325 | 11/1991 | Grell et al. | 514/215 |
| 5,112,838 | 5/1992 | Perregaard et al. | 514/323 |
| 5,216,001 | 6/1993 | Perregaard et al. | 514/253 |

FOREIGN PATENT DOCUMENTS 247250  9/1962  Australia.
0007258A1  1/1980  European Pat. Off..

(List continued on next page.)

OTHER PUBLICATIONS

Adachi et al. (1985) "Aminohaloborane in Organic Synthesis. IX.[1]) Exclusive Ortho Acylation Reaction of N-Monoaminoalkylani-lines", *Chem. Pharm. Bull.*, vol.33(5), pp. 1826–1835.

Arnt, J. et al. (1989), "In Vivo Pharmacology of Irindalone, a 5-HT$_2$ Receptor Atanagonist With Predominant Peripheral Effects", *Drug Develop. Res.*, vol. 16, pp. 59–70.

(List continued on next page.)

*Primary Examiner*—Emily Bernhardt
*Attorney, Agent, or Firm*—Darby & Darby

[57] ABSTRACT

The subject invention relates to 5-Substituted trans-1-piperazinoindan derivatives having general formula (I),

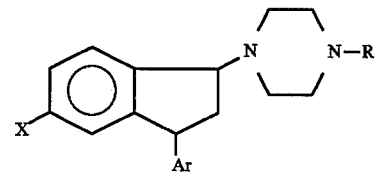

wherein X is halogen, trifluromethyl, alkyl, alkylthio, alkyloxy, hydroxy, alkylsulphonyl, alkyl- or dialkylamino, triflouromethylthio or cyano; R is hydrogen, or alkyl, alkenyl, cycloalkyl, cycloalkyl lower alkyl, optionally substituted with hydroxy, or R is a substituent,

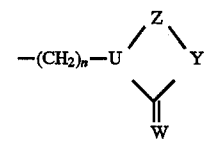

wherein n is an integer from 1 to 6; U is CH or N; Y is, CH$_2$, O, S or N-R$^1$, R$^1$ being hydrogen or cycloalkyl, cycloalkylmethyl, alkyl or alkenyl optionally substituted with hydroxy or an optionally substituted phenyl group; W is O or S; Z is —(CH$_2$)$_4$—,

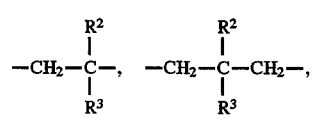

where R$^2$ and R$^3$ are hydrogen or lower alkyl, —CH=CH—, —CH=CH—CH$_2$—, optionally substituted 1,2-phenylene, 1,2-C$_6$H$_4$CH$_2$— (to form a quinazolidinone or -thione ring system) or 1,2-C$_6$H$_4$CO— (to form a quinazolidindion or thixoquinazolidinon ring system); and Ar is an optionally substituted phenyl, thiophene or furane ring; are selective, centrally acting 5-HT$_2$ antagonists useful in the treatment of anxiety, depression, sleeping disorders, negative symptoms of schizophrenia and migraine.

6 Claims, No Drawings

FOREIGN PATENT DOCUMENTS

| | | |
|---|---|---|
| 0112191B1 | 6/1984 | European Pat. Off. |
| 0200322A1 | 11/1986 | European Pat. Off. |
| 0224919A2 | 6/1987 | European Pat. Off. |
| 0259782B1 | 3/1988 | European Pat. Off. |
| 0281309B1 | 9/1988 | European Pat. Off. |
| 0376607B1 | 7/1990 | European Pat. Off. |
| 0392959A2 | 10/1990 | European Pat. Off. |
| 0399982A1 | 11/1990 | European Pat. Off. |
| 0465398A3 | 1/1992 | European Pat. Off. |
| 0470039A2 | 2/1992 | European Pat. Off. |
| 2391211 | 4/1976 | France. |
| 1695604 | 2/1968 | Germany. |
| 2811031 | 3/1978 | Germany. |
| 2827874 | 6/1978 | Germany. |
| 1438094 | 6/1976 | United Kingdom. |
| WO91/09594 | 7/1991 | WIPO. |
| WO92/00070 | 1/1992 | WIPO. |
| WO92/06089 | 4/1992 | WIPO. |

OTHER PUBLICATIONS

Bally et al. (1887) *Chem. Ber.*, vol. 20, p. 2590.

Bøgesø, K. P. et al. (1993), "Stereospecific and Selective 5-HT$_2$ Antagonism in a Series of 5-Substituted trans-1-Piperazino-3-Phenylindans", *J. Med. Chem.*, vol. 36, pp. 2761-2770.

Bøgesø, K. P. et al. (1985), "3-Phenyl-1-indanamines. Potential Antidepressant Activity and Potent Inhibition of Dopamine, Norepinephrine, and Serotonin Uptake", *J. Med. Chem.*, vol. 28, pp. 1817-1828.

Bøgesø, K. P. et al. (1988), "Antihypertensive Activity in a Series of 1-Piperazino-3-phenylindans with Potent 5-HT$_2$-Antagonostic Activity", *J. Med. Chem.*, vol. 31, pp. 2247-2256.

Bøgesø, K. P. (1983), "Neuroleptic Activity and Dopamine-Uptake Inhibition in 1-Piperazino-3-phenylindans", *J. Med. Chem.*, vol. 26, pp. 935-947.

Casini, G. et al. (1969), "On 1,2-Benzisoxazole-3-acetic Acid and 3-Methyl-1,2-Bennzisoxazole: A Restatement", *J. Het. Chem.*, vol. 6, pp. 279-283.

Gladstone et al. (1965), *J. Chem. Soc.*, vol. 7, 3048.

Greuter et al. (1974), *Helv. Chem. Acta*, vol. 57, p. 281.

Hino, T. et al. (1974), "Bromination of 3-Phenylindoles", *Tetrahedron*, vol. 30, pp. 2123-2133.

Hughes, G. K. et al. (1939), "Researchers of Indoles", *J. Proc. Roy. Soc. N.S.Wales*, vol. 72, pp. 209-221.

Hyttel, J. et al. (1985), "Neurochemical Profile of Lu 19-005, a Potent Inhibitor of Uptake of Dopamine, Noradrenaline, and Serotonin", *J. Neurochem*, vol. 44, pp. 1615-1622.

Hyttel, J. et al. (1988), "Neurochemical Profile In Vitro of Irindalone: A 5-HT$_2$-Receptor Antagonist", *Drug. Dev. Res.*, vol. 15, pp. 389-404.

Jones, C.D. (1972), *J. Org. Chem.*, vol. 37, pp. 3624.

LeFur, G. et al. (1977), "Effects of 4-(3-Indolyl-Alkyl)Piperidine Derivatives on Uptake and Release of Noradrenaline, Dopamine and 5-Hydroxytryptamine in Rat Brain Synaptosomes, Rat Heart and Human Blood Platelets", *Biochem. Pharmacol*, vol. 26, pp. 497-503.

Martin et al. (1989), "Activity of Aromatic Substituted Phenylpiperazines Lacking Affinity for Dopamine Binding Sites in a Preclinical Test of Antipsyuchotic Efficacy", *J. Med. Chem.*, vol. 32, pp. 1052-1056.

Mays, R. P. et al. (1980), "Synthesis of 2-Amino-3-Benzoylphenylacetic Acid", *J. Heterocyclic Chem.*, vol. 17, No. 8, pp. 1663-1664.

McElvain, S. M. et al. (1950), "Piperidine Derivatives. XXIII. Certain Halogenated 1-Methyl-4-Phenylpiperidines and Related Compounds", *J. Amer. Chem. Soc.*, vol. 72, pp. 3134-3138.

McMillen, B. A. et al. (1988), "N-Alkyl-Substituted Aryl-Piperazine Drugs: Relationship Between Affinity for Serotonin Receptors and Inhibition of Aggression", *Drug Develop. Res.*, vol. 12, pp. 53-62.

Morooka, S. et al. (1978), "A Convenient Synthesis of 2-Cyano-3-Phenylindoles", *Synthesis*, No. 6, pp. 445 & 446.

Schulenberg, J. W. et al. (1965), "The Chapman Rearrangement", *Organic Reactions*, vol. 14, pp. 1-51.

Perregaard, J. et al. (1992), "Noncataleptogenic, Centrally Acting Dopamien D-2 and Serotonin 5-HT$_2$ Antagonists within A Series of 3-Substituted 1-(4-Fluorophenyl)-1H-indoles", *J. Med. Chem.*, vol. 35, pp. 1092-1101.

Rao, T. S. et al. (1990), "Inhibition of Climbing and Mossy Fiber, and Basket and Stellate Cell Inputs to Mouse Cerebellar Purkinje Cells by Novel Anti-Ischemic Agents, Ifenprodil and BMY-14802", *Life Sciences*, vol. 47, pp. PL-1-PL-5.

Rosenzweig-Lipson, S. et al. (1992), "Stereoselectic Behavioral Effects of Lu 19-005 in Monkeys: Relation to Binding at Cocaine Recognition Sites", *Psychopharmacology*, vol. 107, pp. 186-194.

Sanchez et al. (1991), "Neurochemical and In Vivo Pharmacological Profile of Sertindole, a Limbic-Selective Neuroleptic Compound", *Drug Deve. Res.*, vol. 22, pp. 239-250.

Skarsfeldt, T. et al. (1990), "Sertindole, A New Neuroleptic with Extreme Selectivity on A10 Versus A9 Dopamine Neurones in the Rat", *Eur. J. Pharmacol.*, vol. 182, pp. 613-614.

Szabo-Pusztay et al. (1979), "A Simple General Method for the Oxidation of Indoles to Oxindoles", *Synthesis*, vol. 86, pp. 276-277.

Ueda et al., "Preparation of Piperidinoalkyl Thiazoles as Antiallergic Agents", Chemical Abstract, vol. 107, Abstract No. 236692F (1987).

Yamamoto, H. et al. (1968), "I-Acylindoles. VII.[1]) On Formation Reaction of Indoles from Phenylhydrazines with Several Acidic Catalysts", *Chem. Pharm. Bull.*, vol. 16, No. 12, pp. 2313-2319.

Rao, Tadimeti S. et al. (1990), "BMY-14802 Antagonizes Harmaline-and D-Serine-Induced Increases in Mouse Cerebellar Cyclic GMP: Neurochemical Evidence for a σ Receptor-Mediated Functional Modulation of Responses Mediated by the N-Methyl-D-aspartate Receptor Complex In Vivo", *Molecular Pharmacology*, vol. 37, pp. 978-982.

Martin, PT et al. (1994), "Efficacy and Safety of Sertindole in Two Double-Blind, Placebo-Controlled Trials of Schizophrenic Patients", *Schizophrenia Research*, vol. 11, p. 107.

INDAN DERIVATIVES

This is a continuation of application Ser. No. 08/105,181 filed Jun. 3, 1993, now abandoned which is a continuation of international application Ser. No. PCT/DK91/00358, filed 28 Nov. 1991.

The present invention relates to 5-substituted 1-piperazinoindan derivatives and acid addition salts thereof with selective antagonistic action on the serotonin-2 (5-hydroxytryptamin-2; 5-HT$_2$) receptors in the central nervous system, to medicaments comprising such derivatives as active ingredients, to the use of such derivatives in the treatment of diseases in the central nervous system and to methods for the preparation of such compounds.

The novel piperazinylindan derivatives of the invention are trans-isomers represented by the following Formula I:

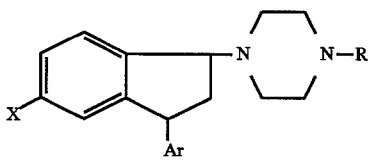

wherein

X is halogen, trifluoromethyl, lower alkyl, lower alkylthio, lower alkoxy, hydroxy, lower alkylsulphonyl, lower alkyl- or dialkylamino, trifluoromethylthio or a cyano group;

R is hydrogen, lower alkyl or alkenyl, cycloalkyl, or cycloalkyl lower alkyl, optionally substituted with one or two hydroxy groups, any hydroxy group present being optionally esterified with an aliphatic carboxylic acid having from two to twentyfour carbon atoms inclusive, or R is a substituent

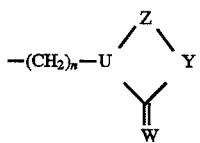

wherein n is an integer from 1 to 6;

U is CH or N;

Y is CH$_2$, O, S or N-R$^1$, R$^1$ being hydrogen or a cycloalkyl or a cycloalkylmethyl or a lower alkyl or alkenyl group optionally substituted with one or two hydroxy groups or a phenyl group optionally substituted with halogen, trifluoromethyl or lower alkyl;

W is O or S;

Z is —(CH$_2$)$_4$—,

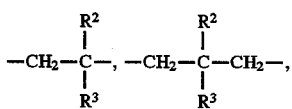

where R$^2$ and R$^3$ are hydrogen or lower alkyl, —CH=CH—CH$_2$—, —CH=CH—, 1,2-phenylene, optionally substituted with halogen or trifluoromethyl, or if U is nitrogen and Y is NR$^1$ Z may also be 1,2-C$_6$H$_4$CH$_2$— (to form a quinazolidinone or -thione ting system) or 1,2-C$_6$H4CO— (to form a quinazolidindion or thioxoquinazolidinon ring system); and Ar is a phenyl ring optionally substituted with halogen, trifluoromethyl or lower alkyl or Ar is a thiophene or furane ring optionally substituted with lower alkyl.

The term "lower alkyl" is intended to mean a straight or branched alkyl group having from one to four carbon atoms, such as methyl, ethyl, n-propyl, iso-propyl, n-butyl, sec-butyl, etc. Lower alkoxy, lower alkylthio, lower alkylsulfonyl, lower alkylamino and lower dialkylamino similarly designate such groups wherein the alkyl moiety is a lower alkyl group as defined above.

Lower alkenyl is intended to mean an alkenyl group containing from 2 to 4 carbon atoms, for example ethenyl, 1-propenyl, 2-butenyl, etc.

Cycloalkyl is intended to mean cycloalkyl having from 3 to 8 carbon atoms incl. in the ring.

The Z-group may be oriented in both directions in the ring.

Halogen means fluoro, chloro, bromo or iodo.

When Y is NR$^1$ wherein R$^1$ is H, the compound may exist in tautomeric form, i.e. wherein W is —OH or —SH, respectively, connected to the ring via a single bond, and having a double bond in the ring, i.e. from the Y to the carbon atom bearing the —OH or —OS group. Such tautomeric forms are intended to be embraced by Formula I.

Compounds similar to the compounds of the present invention are disclosed in our own U.S. Pat. No. 4,443,448 which relates to 1-piperazino-3-phenylindan derivatives having one substituent in the benzen moiety of the indan ring system and claimed to have neuroleptic or antidepressant activity. The neuroleptic activity of the compounds is based on tests showing dopamine antagonistic activity in vivo whereas antidepressant activity is shown by the ability of the compounds to inhibit the reuptake of dopamine. A number of the compounds of the general Formula I of the present invention are generically embraced by the general scope of said patent. However, only a few of the 5-substituted derivatives of the general Formula I of the present invention are specifically mentioned in said patent. All of said compounds are compounds of the general Formula I wherein Ar is 4-fluorophenyl R is lower alkyl optionally substituted with hydroxy. Only some of said compounds were tested and they were all found to be without significant activity as dopamine antagonists in the in vivo test used, cf. Table 8 of said patent. Accordingly they were regarded to be without value as neuroleptics. No results as to dopamine reuptake inhibiting effects are given for those compounds.

Our own U.S. Pat. No. 4,684,650 discloses a series of optionally 6-substituted 1-piperazino-3-phenylindans claimed to have a potent antiserotonergic activity without having any significant neuroleptic activity. It was shown that the compounds had a high affinity to 5-HT$_2$ receptors whereas they were weak or inactive in an in vivo model for antidopaminergic effect, i.e. the methylphenidate antagonism test. Many of the compounds were shown to have potent antihypertensive action. In a later publication about the same series of compounds (K. P. Bøgesø et al., J. Med. Chem., 1988, 31,2247) it was shown that in despite of a selective antiserotonergic profile in vivo, nevertheless many of the compounds still had significant activity for both dopamine D-2 receptors and in particular α$_1$ adrenoceptors.

The 5-HT$_2$ antagonist ritanserin (Meert, T. F.; Janssen, P. A. J. Drug. Dev. Res. 1989, 18, 119.) has been shown to be effective in the treatment of anxiety and depression presumably through improvement of the sleep quality. Furthermore, selective, centrally acting 5-HT$_2$ antagonists have been shown to have an effect towards the negative symptoms of schizophrenia and to reduce extra-pyramidal side-effects caused by treatment with classical neuroleptics in schizophrenic patients (Gelders, Y. G., British J. Psychiatry, 1989, 155 (suppl. 5), 33). Finally, selective 5-HT$_2$ antagonists could be effective in the prophylaxis of migraine since it is known that 5-HT is involved in migraine attacks. The links between 5-HT and migraine attacks are several and they suggest a number of mechanisms whereby 5-HT may be involved (Scrip Report; "Migraine—Current trends in research and treatment"; PJB Publications Ltd.; May 1991 ). Various 5-$HT_2$ antagonists are in clinical trials as anti-migraine agents, such as sergolexole (c.f. for example Pharma Projects, May 1991, 1359–1365). Obviously there is a strong demand for selective 5-$HT_2$ antagonists without side effects.

It has now surprisingly been found that the 5-substituted 1-piperazinoindan derivatives of Formula I, have high affinity for 5-$HT_2$ receptors. As compared to the corresponding 6-substituted derivatives they have very low affinity to both dopamine D-2 receptors and $\alpha_1$ adrenoceptors. In vivo the compounds have potent activity in animal models for central 5-$HT_2$ antagonism. Because of the very low affinity for adrenoceptors the 5-substituted compounds have, in contrast to the 6-substituted derivatives, substantially no effect on the blood pressure.

Only trans-isomers of the 5-substituted 1-piperazinoindan derivatives of Formula I are active, cis-isomers being without significant 5-$HT_2$ antagonistic activity.

Accordingly in a first aspect the present invention relates to trans-isomers of the compounds having the general Formula I as defined above and pharmaceutically acceptable acid addition salts thereof and prodrugs therefore with the proviso that R may not be hydrogen or lower alkyl or alkenyl optionally substituted with hydroxy when Ar is optionally substituted phenyl.

The trans-isomers of the invention exist as pairs of optically active isomers and such isomers are within the scope of the present invention. Also any other stereoisomer of a compound having the general Formula I is embraced by the invention. It has so far been found that the 5-$HT_2$ antagonistic activity predominantly resides in one of the optical isomers.

Prodrugs of the present invention may be conventional esters when hydroxy groups are available, or in particular if the compound is a compound of the general Formula I wherein W is O and Y is $NR^1$, $R^1$ being hydrogen, the prodrug may be a reaction product with an acid or an activated acid, with formaldehyde alone or in the presence of an alcohol or an amine, or with an acyloxymethylene halide, which product accordingly may be represented by a formula similar to the general Formula I defined above wherein W is O, Y however being a group $NR^{1''}$ wherein $R^{1''}$ designates a group —A—B where A is selected from CO, CS, or $CH_2$, and if A is CO or CS, B is selected from the groups consisting of:

i) hydrogen, alkyl, alkenyl, cycloalkyl, cycloalkenyl or cycloalk(en)ylalk(en)yl, optionally substituted with one or two hydroxy groups, or phenyl optionally substituted with one or more substituents selected from the group consisting of halogen, trifluoromethyl, lower alkyl, lower alkoxy, lower alkylthio, acyloxy, or cyano; or ii) $QB^1$, wherein Q is O or S and $B^1$ is selected from the substituents defined for B under i) above except hydrogen; and iii) $NB^2B^3$, wherein $B^2$ and $B^3$ independently are selected from the substituents defined for $B^1$ under ii) above, or $B^2$ and $B^3$ are combined to form a four to eight membered heterocyclic ring containing from one to three nitrogen atoms and from zero to three oxygen or sulfur atoms; or if A is $CH_2$, B is selected from the groups consisting of:

iv) a group $QB^1$ as defined in ii);

v) a group $NB^2B^3$ as defined in iii); or vi) a group $OC(O)B^4$, wherein $B^4$ is as defined for $B^1$.

Although the latter prodrugs are not esters they would decompose properly in order to release the compound of the invention over a desired period of time when administered parenterally as a depote formulation in an apropriate oil, such as coconut oil, e.g. viscoleo®, peanut oil, sesame oil, cotton seed oil, corn oil, soy bean oil, olive oil, etc. or synthetic esters of fatty acids and glycerol or propylenglycol.

The pharmaceutically acceptable acid addition salts of the compounds used in the invention are salts formed with non-toxic organic or inorganic acids. Exemplary of such organic salts are those with maleic, fumaric, benzoic, ascorbic, embonic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, steadc, palmitic, itaconic, glycolic, p-amino-benzoic, glutamic, benzene sulfonic and theophylline acetic acids, as well as the 8-halotheophyllines, for example 8-bromo-theophylline. Exemplary of such inorganic salts are those with hydrochloric, hydrobromic, sulfuric, sulfamic, phosphoric and nitric acids.

The compounds of the invention show high affinity to 5-$HT_2$ receptors and very low receptor affinity to D-2 receptors and $\alpha_1$ adrenoceptors and consequently they are very selective with respect to the 5-$HT_2$ receptor. Accordingly, they are useful in the treatment of varios diseases of the central nervous system, such as anxiety, depression, sleeping disorders, negative symptoms of schizophrenia, extrapyramidal side-effects caused by treatment with classical neuroleptics, and migraine.

Preferred 5-substituted trans-1-piperazinoindan derivatives according to the invention are those wherein:

Ar is a phenyl ring optionally substituted with halogen or methyl, preferably 4-fluorophenyl; X is Cl or F and/or R is a group of the formula:

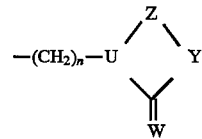

wherein n is 2,

U is nitrogen; W is O or S; Z is —$CH_2$—$CH_2$— or —$CH_2$—$CH_2$—$CH_2$—; and

Y is a group $NR^1$ wherein $R^1$ is hydrogen or lower alkyl.

Most preferably the compound of the invention is selected from the group of:

(−)-Trans-1-[2-[4-[5-chloro-3-(4-fluorophenyl)-2,3-dihydro-1H-inden-1-yl]piperazin-1-yl]-ethyl]-3-isopropyl-2-imidazolidinone, dimaleate;

(+)-Trans-1-[2-[4-[5-fluoro-3-(4-fluorophenyl)-2,3-dihydro-1H-inden-1-yl]piperazin-1-yl]ethyl]-tetrahydro-2(1H)-pydmidinethione,dihydrochloride;

(−)-Trans-1-[2-[4-[5-chloro-3-(4-fluorophenyl)-2,3-dihydro-1H-inden-1-yl]piperazin-1-yl]ethyl]-tetrahydro-2(1H)-pyrimidinethione,dihydrochloride;

(+)-Trans-1-[2-[4-[5-fluoro-3-(4-fluorophenyl)-2,3-dihydro-1H-inden-1-yl]piperazin-1-yl]ethyl]-tetrahydro-2(1H)-pyrimidinone,dimaleate; and (−)-Trans- 1-[2-[4-[5-chloro-3-(4-fluorophenyl)-2,3-dihydro-1H-inden-1-yl]piperazin-1-yl]ethyl]-tetrahydro-2(1H)-pyrimidinone,dimaleate.

In a second aspect the present invention relates to a pharmaceutical preparation comprising at least one derivative of the general Formula I as defined above together with a pharmaceutically acceptable carrier or diluent.

The compounds of the Formula I and the pharmaceutically acceptable acid addition salts thereof may be administered by any suitable route, for example orally in the form of tablets, capsules, powders, syrups, etc., or parenterally in the form of solutions for injection.

Suitable pharmaceutical preparations may be prepared by methods well known in the art. Conveniently, the compounds of the invention are administered in unit dosage form containing said compound in an amount of about 0.05–100 mg, preferably about 1–50 mg.

The total daily dose usually ranges from about 0.1 to 500 mg of the active compound of the invention.

In a further aspect the present invention relates to the use of a compound having the general Formula I as defined above for the manufacture of a medicament for the treatment of a disease in the central nervous system, preferably anxiety, depression, sleeping disorders, negative symptoms of schizophrenia, extrapyramidal side-effects caused by treatment with classical neuroleptics, and migraine.

The invention moreover relates to a method for the preparation of the novel 5-substituted derivatives of Formula I, which comprises:

a) treating a compound of the following Formula II:

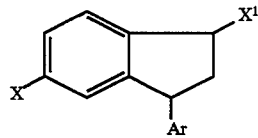

with a piperazine derivative of formula:

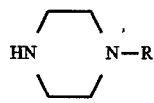

in which formulas X, Ar and R are as defined above, and $X^1$ is halogen or $-OSO_2R^4$ wherein $R^4$ is alkyl such as $CH_3$ or aryl such as p-toluyl;

b) treating a compound of the following Formula III:

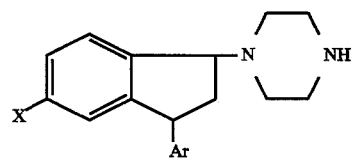

wherein X and Ar are as defined above, with a compound of the formula $X^1$—R wherein R and $X^1$ are as defined above except that R cannot be hydrogen;

c) treating a compound of Formula III with a compound R'—CHO, wherein R' is such a group that R'—CH$_2$— is as defined above for R, in the presence of a reducing agent;

d) treating a compound of the following Formula IV:

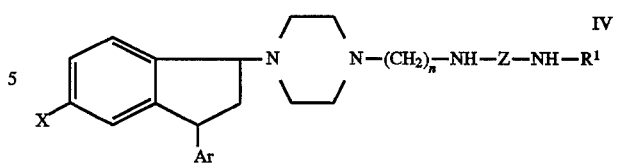

wherein X, Ar, $R^1$, Z and n are as defined above, with $CS_2$, thiophosgene, urea or phosgene;

e) treating a compound of the following Formula V:

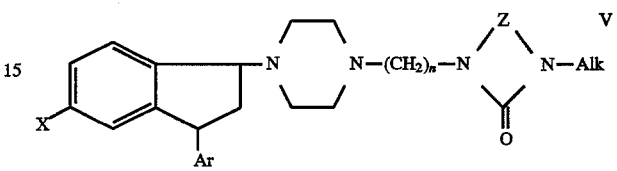

wherein X, Ar, n, and Z are as defined above, and $X^1$ is an alkali metal such as sodium or potassium, with a compound of formula $R^5$-$X^1$ wherein $R^5$ is a lower alkyl group and $X^1$ is as defined above;

f) reducing a compound with the following Formula VI:

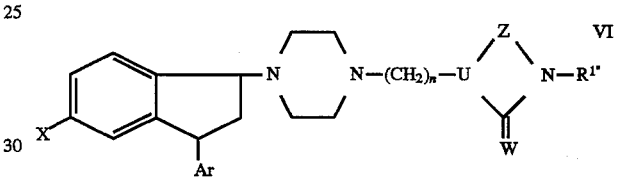

wherein X, Ar, n, U, Z and W are as defined above and $R^{1'''}$ is a cycloalkyl or lower alkyl group containing one or more ester, ketone or aldehyde groups, with a suitable reducing agent to a corresponding compound wherein $R^1$ is a lower alkyl or a cycloalkyl group containing one or more hydroxy groups;

g) reacting a compound of Formula I wherein R is a group of the formula:

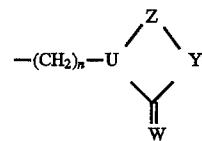

wherein n, U, Z and Y are as defined above an W is O, with $P_2S_5$ or Lawessons reagent to obtain the corresponding compound wherein W is S.

Method a) is preferably carried out in an inert solvent such as acetone or methylisobutylketone using either an excess of the piperazine reactant or by using equimolar amounts of reactants in the presence of an alkali metal carbonate such as potassium carbonate or another alkaline substance at reflux temperatures.

Method b) is preferably carried out in an inert solvent such as ethanol or isobutylketone in the presence of an alkali metal carbonate such as potassium carbonate or another alkaline substance at reflux temperatures.

Method c) is preferably carried out in an inert solvent such as an alcohol (eg methanol) or an ether (eg tetrahydrofuran) by hydrogenation in the presence of a suitable catalyst such as Pt or Pd or by using a borohydride such as NaCNBH$_3$ at a pH of 5–6.

Method d) is preferably carried out by treating a compound of Formula IV in an inert solvent, such as n-pentanol or n-butanol, with urea or carbon disulfide succeeded by heating at reflux temperatures.

In Method e), the alkalimetal salt of Formula V is preferably formed by treating the corresponding hydrogen derivative with an alkali metal alkoxide such as potassium tert.-butoxide in an inert solvent such as toluene whereupon the salt is reacted directly with the alkylating agent, $R^5-X^1$, at room or higher temperatures.

Method f) is preferably carried out by reducing the derivative of Formula Vi with a suitable reducing agent such as lithium or sodium borohydride in an inert solvent such as tetrahydrofurane.

Method g) is preferably carried out in hexamethyl phosphorous triamide (HMPA) or xylene at temperatures between 110° C. and 200° C.

The acid addition salts of the compounds of the invention are easily prepared by methods well known in the art. The base is reacted with either the calculated amount of organic or inorganic acid in an aqueous miscible solvent, such as acetone or ethanol, with isolation of the salt by concentration and cooling, or with an excess of the acid in an aqueous immiscible solvent, such as ethyl ether or chloroform, with the desired salt separating directly. Of course, these salts may also be prepared by the classical method of double decomposition of appropriate salts.

The preparation of the compounds of Formula II from the corresponding 2,3-dihydroinden-1-ones may be carried out analogueously with the method described in U.S. Pat. No. 4,443,448, U.S. Pat. No. 4,684,650, and J. Med. Chem. 1983, 26, 935. The indanones were either prepared by cyclization of the corresponding diphenylpropionic acids or more conveniently as described for similar compounds in U.S. Pat. No. 4,873,344 and in J. Org. Chem. 1990, 55, 4822 from the proper 3,5-disubstituted 1-amino-3-cyano-1-inden-2-carboxylic acid esters which in turn also may be prepared as described in U.S. Pat. No. 4,873,344. Hereby the following novel 3,5-disubstituted 1-amino-3-cyano-1-inden-2-carboxylic acid esters were prepared:

1-Amino-3-cyano-3-(4-fluorophenyl)-5-methyl-1-inden-2-carboxylic acid methyl ester, mp 215°–217° C.
1-Amino-5-chloro-3-cyano-3-phenyl-1-inden-2-carboxylic acid methyl ester, mp 192°–194° C.
1-Amino-5-chloro-3-cyano-3-(2-fluorophenyl)-1-inden-2-carboxylic acid methyl ester, mp 227°–228° C.
1-Amino-5-chloro-3-cyano-3-(3-fluorophenyl)-1-inden-2-carboxylic acid methyl ester, mp 191°–193° C.
1-Amino-5-chloro-3-cyano-3-(2-methyl-4-thienyl)-1-inden-2-carboxylic acid methyl ester, mp 161°–163° C.
1-Amino-5-chloro-3-cyano-3-(4-chlorophenyl)-1-inden-2-carboxylic acid methyl ester, mp 213°–215° C.
1-Amino-5-chloro-3-cyano-3-(4-methylphenyl)-1-inden-2-carboxylic acid methyl ester, mp 228°–230° C.

By the above method the following novel 2,3-dihydro-1H-inden-1-ones were prepared:

3-(4-fluorophenyl)-5-(trifluoromethyl)-2,3-dihydro-1H-inden-1-one, mp105°–106° C.
3-(4-fluorophenyl)-5-methyl-2,3-dihydro-1H-inden-1-one, mp 69°–71° C.
5-chloro-3-phenyl-2,3-dihydro-1H-inden-1-one, mp 127°–129° C.
5-chloro-3-(2-fluorophenyl)-2,3-dihydro-1H-inden-1-one, mp 83°–85° C.
5-chloro-3-(3-fluorophenyl)-2,3-dihydro-1H-inden-1-one, mp 118°–120° C.
3-(4-fluorophenyl)-5-methylthio-2,3-dihydro-1H-inden-1-one, mp 74°–76° C.
5-chloro-3-(2-methyl-4-thienyl)-2,3-dihydro-1H-inden-1-one, mp 101°–102° C.
5-chloro-3-(4-chlorophenyl)-2,3-dihydro-1H-inden-1-one, mp 140°–142° C.
5-chloro-3-(4-methylphenyl)-2,3-dihydro-1H-inden-1-one, mp 112°–114° C.

As previously described (see references cited above) the 2,3-dihydro-1H-inden-1-ones may be reduced with sodium borohydride to the corresponding cis-2,3-dihydro-H-inden-1-ols which serves as the starting materials for preparing the compounds of Formula II. The following new 2,3-dihydro-1H-inden-1-ols were obtained:

3-(4-fluorophenyl)-5-(trifluoromethyl)-2,3-dihydro-1H-inden-1-ol, mp 81°–83° C.
3-(4-fluorophenyl)-5-methyl-2,3-dihydro-1H-inden-1-ol, mp 100°–102° C.
5-chloro-3-phenyl-2,3-dihydro-1H-inden-1-ol, mp 110°–111° C.
5-chloro-3-(2-fluorophenyl)-2,3-dihydro-1H-inden-1-ol, mp 78°–80° C.
5-chloro-3-(3-fluorophenyl)-2,3-dihydro-1H-inden-1-ol, mp 110°–112° C.
3-(4-fluorophenyl)-5-methylthio-2,3-dihydro-1H-inden-1-ol, mp 114°–116° C.
5-chloro-3-(2-methyl-4-thienyl)-2,3-dihydro-1H-inden-1-ol, mp 119°–121° C.
5-chloro-3-(4-chlorophenyl)-2,3-dihydro-1H-inden-1-ol, mp 129°–131° C.
5-chloro-3-(4-methylphenyl)-2,3-dihydro-1H-inden-1-ol, mp 107°–109° C.

In the following, the invention is further illustrated by way of examples which must in no way be construed as limiting for the invention.

EXAMPLES

EXAMPLE 1

Trans -1-[2-[4-[3-(4-fluorophenyl)-5-(trifluoromethyl)-2,3-dihydro-1H-inden-11-yl]-1-piperazinyl]ethyl]-2-imidazolidinone, dimaleate (Compd. 1)

A mixture of 1-Chloro-3-(4-fluorophenyl)-5-(trifluoromethyl)-2,3-dihydro-1H-inden (8.5 g) and 1-[(2-(piperazin-1-yl)ethyl]-2-imidazolidinone (20 g) in methylisobutylketone (250 ml) was stirred at 80° C. for 18 hours.

The reaction mixture was cooled, whereupon ether and water was added. The phases were separated, and the organic phase was washed with water. The ether phase was extracted with 1 N methane sulphonic acid. The base was liberated with 10 N sodium hydroxide and extracted with methylene chloride. The organic phase was dried (MgSO$_4$) and evaporated in vacuo to give 10 g of crude 1. The crude base was dissolved in acetone and transformed to the maleate salt which was recrystallized from ethanol (100 ml) to give 4.9 g of 1, as dimaleate; mp 169°–171° C.

CHN calculated: 55.92%; 5.13%; 7.91%. CHN found: 55.94%; 5.02%; 7.94%.

EXAMPLE 2

Preparation of (+)-1 (the active enantiomer of 1)

To a solution of trans-1-[3-(4-fluorophenyl)-5-(trifluoromethyl)-2,3-dihydro-1H-inden-1-yl]piperazine (38 g) in ethanol (500 ml) was added a solution of L-(+)-tartaric acid (15 g) in water (25 ml). The mixture was left overnight at room temperature. The crystals were filtered and recrystallized from mehanol (400 ml) and water (400 ml) to give 17 g; mp 221°–223° C. Optical rotation of the base: $[\alpha]_D = -3.2°$ (c0.5, MeOH).

The first filtrate from the L-(+)-tartrate salts was evaporated in vacuo and convened to the base. This base (25 g) was dissolved in methanol (400 ml) and a solution of D-(−)tartaric acid (10 g) in water (50 ml) was added. The mixture was kept for 2 hours at room temperature. The crystals were filtered and recrystallized from methanol (250 ml) and water (250 ml) to give 13 g, mp 222°–224° C. Optical rotation of the base: $[\alpha]_D = +3.7°$ (c0.5, MeOH).

The D-(−)-tartrate salt was convened to the base (9.5,g) which was added to a mixture of 1-(2-chloroethyl)-2-imidazolidinone (9 g), potassium carbonate (10 g) and potassium iodide (0.5 g) in methylisobutylketone (250 ml). The mixture was refluxed with stirring for 18 hours. The reaction mixture was worked up as described in Example 1, to give a crude base (15 g). The base was converted to the dimaleate salt which was recrystallized three times from ethanol to give (+)-1, dimaleate salt, mp 158°–159° C. $[\alpha] = +5,5°$ (c0.5, $CH_3OH$).

CHN calculated: 55.92%; 5.13%; 7.91%. CHN found: 55.92%; 5.09%; 7.95%.

EXAMPLE 3

Optical resolution of Trans-4-[5-fluoro-3-(4-fluorophenyl)-2,3-dihydro-1H-inden-1-yl]-1-piperazine ethanol (Compd. 2)

The dihydrochloride salt of Compd. 2 (11 g, c.f. U.S. Pat. No. 4,443,448) was converted to the base (9.5 g). A solution of the base and L-(+)-tartaric acid (4 g) in ethanol (250 ml) was kept at room temperature for 18 hours. The crystals were filtered off and dried (4.5 g), and recrystallized from methanol (600 ml) to give 3.2 g; mp 216°–217° C.; $[\alpha]_D = +15.4°$ (c0.5, DMSO). The L-(+)-tartrate salt was converted to the base, which was transferred to the dihydrochloride salt. The dihydrochloride salt was recrystallized from ethanol/ether to give 1 g of (+)-2, dihydrochloride; mp 224°–226° C.; $[\alpha]_D = +27.1°$ (c0.5, $CH_3OH$).

The first filtrate from the L-(+)-tartrate salt was evaporated and converted to the base. The base was converted to the D-(−)-tartaric salt which was recrystallized and converted to the dihydrochloride salt as described for (+)-2.

0.6g of (−)-2, dihydrochloride was obtained; mp 223°–226° C.; $[\alpha]_D = -27.1°$ (c0.5, $CH_3OH$), Trans-4-[5-chloro-3-(4-fluorophenyl)-2,3-dihydro-1H-inden-1-yl)-1-piperazine-ethanol (3, c.f. U.S. Pat. No. 4,443, 448) was resolved in a similar way to give (+)-3, dihydrochloride; mp 224°–227° C.; $[\alpha]_D = +13.5°$ (c0.5, $H_2O$) and (−)-3, dihydrochloride; mp 224°–227° C.; $[\alpha]_D = -14.1°$ (c0.5, $H_2O$).

The method described in Example was used for the preparation of the following compounds:

Trans-1-[2-[4-[5-chloro-3-(4-fluorophenyl)-2,3-dihydro-1H-inden-1-yl]piperazine-1-yl]ethyl]-2-imidazolidinone; mp 168°–170° C. Compd. 4.

Trans-4-[3-(4-fluorophenyl)-5-(trifluoromethyl)-2,3-dihydro-1H-inden-1-yl]-1-piperazineethanol, dimaleate; mp 172°–174° C. Compd. 5.

Trans-4-[5-chloro-3-(2-methyl-4-thienyl)-2,3-dihydro-1H-inden-1-yl]-1-piperazineethanol, dimaleate; mp 175°–177° C. Compd. 6.

Trans-1-[2-[4-[5-chloro-3-(2-methyl-4-thienyl)-2,3-dihydro-1H-inden-1-yl]piperazine-1-yl]ethyl]-2-imidazolidinone, dimaleate; mp 174°–176° C. Compd. 7.

Trans-4-[3-(4-fluorophenyl)-5-methyl-2,3-dihydro-1H-inden- 1-yl]- 1-piperazine ethanol, dimaleate; mp 169°–171° C. Compd. 8.

Trans-1-[2-[4-[3-(4-fluorophenyl)-5-methyl-2,3-dihydro-1H-inden-1-yl]piperazine-1-yl]ethyl]-2-imidazolidinone, dimaleate; mp 180°–181° C. Compd. 9.

EXAMPLE 4

Trans-1-[5-chloro-3-(4-fluorophenyl)-2,3-dihydro-1H-inden- 1-yl]piperazine, maleate (Compd. 10)

Thionylchloride (44 ml) was added dropwise with water-cooling to a solution of 5-chloro-3-(4-fluorophenyl)-2,3-dihydro-1H-inden-1-ol in ether (2L) with a catalytic amount of DMF (0.5 ml). Then the mixture was stirred for 2 hours at room temperature, poured into ice and neutralized with 9N NaOH. The organic phase was separated, dried ($MgSO_4$) and evaporated to give 140 g of crude 1,5-dichloro-3-(4-fluorophenyl)-2,3-dihydro-1H-inden.

A mixture of the chloroderivative (140 g), piperazine (800 g) and acetone (2L) was refluxed with stirring for 18 hours. After cooling piperazine hydrochloride was filtered off and washed with ethyl acetate. The combined filtrate was concentrated in vacuo. The residue was dissolved in ether, washed with water and extracted with 1N methane sulphonic acid. The base was liberated from the acid extract with 9N sodium hydroxide, extracted with ether, dried ($MgSO_4$) and evaporated in vacuo to give crude Compd. 10 (156 g). The residue was dissolved in acetone (600 ml) and ethanol (600 ml), whereupon maleic acid (110 g) was added. After 1 hour at room temperature the maleate salt of Compd. 10 was filtered and dried. Yield: 216 g; mp 190°–191° C.

10 g were recrystallized from ethanol to give pure Compd. 10, maleate; mp: 194°–195° C.

CHN calculated: 61.81%; 5.42%; 6.27%. CHN found: 61.77%; 5.40%; 6.34%.

EXAMPLE 5

Optical resolution of Compd. 10 ((+)-10 and (−)-10)

A solution of Compd. 10 (24 g) and (−)-dibenzoyl-L-tartaric acid hydrate ((−)DBT) (27.3 g) in acetone (250 ml) was left for 18 hours at room temperature. The crystals were filtered and dried. The (−)DBT salt was boiled with methanol (1L), cooled, filtered and dried to give 13.5 g of (−)-DBT salt; mp: 213°–214° C.

The first filtrate from the (−)-DBT salt was concentrated and converted to the base (13 g), which was treated with (+)-DBT in the same manner as described for the (−)-DBT salt. Yield: 11 g of (+)-DBT salt; mp: 212°–213° C.

The DBT salts were converted to the bases and then precipitated as maleate salts. The maleate salts were recrystallized from ethanol (200 ml) and methanol (50 ml) to give (+)-10, maleate salt; mp: 194°–196° C.; $[\alpha]_D = +30.6°$ (c0.5, $CH_3OH$). (−)-10, maleate salt; mp: 194°–196° C.; $[\alpha]_D = 30.2°$ (c0.5, $CH_3OH$).

EXAMPLE

Trans-1-[2-[4-[5-chloro-3-(4-fluorophenyl)-2,3-dihydro-1H-inden-1-yl]piperazin-1-yl]-ethyl]-3-isopropyl-2-imidazolidinone, dimaleate (Compd. 11)

A mixture of Compd. 10 (140 g as the maleate salt, see Example 4), 1-(2-chloroethyl)-3-isopropyl-2-imidazolidinone (75 g), potassium carbonate (260 g) and potassium iodide (5 g) in methylisobutylketone (1 L) was refluxed with stirring for 18 hours.

After cooling, water (500 ml) was added. The phases were separated and the organic layer was washed with water and then concentrated in vacuo. The residue was dissolved in ether, washed with water and extracted with 1N methane sulphonic acid. The base was liberated with 9N NaOH, extracted with ether, dried and concentrated in vacuo to give 157 g of crude Compd. 11. The base was converted to the dimaleate salt in ethanol (2L) to give 193 g of trans-isomer (11).

A sample recrystallized from methanol melted at 188°–190° C.

CHN calculated: 58.61%; 5.92%; 7.81%. CHN found: 58.78%; 5.90%; 7.88%.

EXAMPLE 7

Optical resolution of Compd. 11 ( (+)-11 and (–)-11)

The resolution was performed essentially as described in the Examples 2 and 3 (using L-(+)- and D-(–)-tartaric acid) with the exception that tartrate salts were crystallized and recrystallized from water. From 126 g of 11 (as the base) there was obtained 50 g of D-(–)-tartrate, mp 102°–104° C., and 51 g of L-(+)-tartrate, mp 102°–104° C.

In a conventional manner the tartrate salts were converted to the maleate salts which were recrystallized from ethanol to give
(+)-11, dimaleate, mp 175° C., $[\alpha]_D$=+17.0° (c0.5, $CH_3OH$), and
(–)-11, dimaleate, mp 175° C., $[\alpha]_D$=–17.5° (c0.5, $CH_3OH$).

The method described in Example 6 was used for the preparation of the following compounds:

Trans-1-[2-[4-[3-(4-fluorophenyl)-5-methyl-2,3-dihydro-1-H-inden-1-yl]piperazin-1-yl]ethyl]-3-isopropyl-2-imidazolidinone,dimaleate; mp 178°–180 ° C. Compd. 12.

Trans-1-[2-[4-[3-(4-fluorophenyl)-5-(trifluoromethyl)-2,3-dihydro-1H-inden-1-yl]piperazin-1-yl]ethyl]-3-isopropyl-2-imidazolidinone, dimaleate; mp 174°–176° C. Compd. 13.

Trans-3-[2-[4-[5-chloro-3-(4-fluorophenyl)-2,3-dihydro-1-H-inden-1-yl]piperazin-1-yl]ethyl]-2-oxazolidinone, diHCl; mp 244°–246° C. Compd. 14.

Trans-1-[2-[4-[5-chloro-3-(4-fluorophenyl)-2-3-dihydro-1-H-inden-1-yl]piperazin-1-yl]ethyl]-2-pyrrolidinone, diHCl; mp 250°–252° C. Compd. 15.

Trans-1-[3-[4-[5-chloro-3-(4-fluorophenyl)-2,3-dihydro-1-H-inden-1-yl]piperazin-1-yl]propan-1-yl]-2-imidazolidinone,dimaleate; mp 159°–160° C. Compd. 16.

Trans-1-[2-[4-[5-chloro-3-(4-fluorophenyl)-2,3-dihydro-1H-inden-1-yl]piperazin-1-yl]ethyl]-3-phenyl-2-imidazolidinone,dimaleate; mp 174°–176° C. Compd. 17.

Trans-1-[2-[4-[5-chloro-3-(4-fluorophenyl)-2,3-dihydro-1H-inden-1-yl]piperazin-1-yl]ethyl]-3-methyl-2-imidazolidinone:dimaleate; mp 164°–166° C. Compd. 18.

Trans-1-[2-[4-[5-chloro-3-(4-fluorophenyl)-2,3-dihydro-1H-inden-1-yl]piperazin-1-yl]ethyl]-3-ethyl-2-imidazolidinone,dimaleate; mp 178°–180° C. Compd. 19.

Trans-1-[2-[4-[5-chloro-3-phenyl-2,3-dihydro-1H-inden-1-yl]piperazin-1-yl]ethyl]-3-isopropyl-2-imidazolidinone, dimaleate; mp 189°–190 ° C. Compd. 20.

Trans-1-[2-[4-[5-chloro-3-(2-fluorophenyl)-2,3-dihydro-1H-inden-1-yl]piperazin-1-yl]ethyl]-3-isopropyl-2-imidazolidinone,dimaleate; mp 190°–192° C. Compd. 21.

Trans-1-[2-[4-[3-(4-fluorophenyl)-5-(methylthio)-2,3-dihydro-1H-inden-1-yl]piperazin-1-yl]ethyl]-2-imidazolidinone,dimaleate; mp 182°–184° C. Compd. 22.

Trans-1-[2-[4-[3-(4-fluorophenyl)-5-(methylthio)-2,3-dihydro-1H-inden-1-yl]piperazin-1-yl]ethyl]-3-isopropyl-2-imidazolidinone,dimaleate; mp 186°–188° C. Compd. 23.

Trans-1-[2-[4-[5-bromo-3-(4-fluorophenyl)-2,3-dihydro-1H-inden-1-yl]piperazin-1-yl]ethyl]-3-isopropyl-2-imidazolidinone,dimaleate; mp 180°–182° C. Compd. 24.

Trans-1-[2-[4-[5-chloro-3-(4-fluorophenyl)-2,3-dihydro-1H-inden-1-yl]piperazin-1-yl]ethyl]-benzimidazolin-2-one,dimaleate; mp 192°–194° C. Compd. 25.

Trans-1-[2-[4-[5-chloro-3-(4-methylphenyl)-2,3-dihydro-1H-inden-1-yl]piperazin-1-yl]ethyl]-3-isopropyl-2-imidazolidinone,dimaleate; mp 184°–186° C. Compd. 26.

Trans-1-[2-[4-[5-chloro-3-(4-chlorophenyl)-2,3-dihydro-1H-inden-1-yl]piperazin-1-yl]ethyl]-3-isopropyl-2-imidazolidinone,dimaleate; mp 170°–172° C. Compd. 27.

Trans-1-[2-[4-[5-chloro-3-(3-fluorophenyl)-2,3-dihydro-1H-inden-1-yl]piperazin-1-yl]ethyl]-3-isopropyl-2-imidazolidinone,dimaleate; mp 180°–182° C. Compd. 28

EXAMPLE 8

Trans-1-[2-[4-[5-fluoro-3-(4-fluorophenyl)-2,3-dihydro-1H-inden-1-yl]piperazin-1-yl]-ethyl]-2-imidazolidinthione, dimaleate (Compd. 29)

A mixture of Compound 2 (140 g, base, c.f. U.S. Pat. No. 4,443,448), thionyl chloride (100 ml) and DMF (10 ml)in chloroform (2L) was refluxed for 2 hours. After cooling, the hydrochloride salt of the chloroethyl derivative of 2 was filtered, washed with ethyl acetate and dried (Yield: 84 g).

A mixture of 42 g of the hydrochloride salt and ethylendiamine (100 ml) in ethanol (500 ml) was refluxed with stirring for 3 hours. The mixture was concentrated in vacuo; the residue was dissolved in a mixture of methylene chloride and water, the organic layer was separated, washed with saturated NaCl solution, dried ($MgSO_4$) and evaporated in vacuo to give 40 g of crude trans-1-[5-fluoro-3-(4-fluorophenyl)-2,3-dihydro-1H-inden-1-yl]-4-[2-[(2-aminoethyl)amino]ethyl]piperazine as an oil. Said ethylendiamine derivative was dissolved in methylene chloride, whereupon carbon disulfide (15 ml) was added. The mixture was kept for 1 hour at room temperature, and was then evaporated in vacuo. The crude dithiocarbamate salt was dissolved in n-pentanol and refluxed for 1 hour (evolution of hydrogen sulfide). The reaction mixture was concentrated in vacuo. The residue was dissolved in ether, extracted with 1N methanesulfonic acid, whereupon the base was liberated with 9N NaOH and extracted with ether. The ether solution was filtered through silica gel, and concentrated to yield 24 g of an oil, which was transformed to the dimaleate to give 29, dimaleate, mp 172°–174° C.

CHN calculated: 57.04%; 5.25%; 8.32%. CHN found: 57.30%; 5.43%; 8.17%.

Trans-1-[2-[4-[5-fluoro-3-(4-fluorophenyl)-2,3-dihydro-1H-inden-1-yl]piperazin-1-yl]ethyl]-tetrahydro-2(1H)-pyrimidinethione,dimaleate. mp 174°–176° C., Compd. 30 was prepared in a similar way, by replacing ethylendiamine with 1.3-propylendiamine. The enantiomers of this compound were prepared in a similar way starting from (+)-2 and (–)-2, respectively:

(+)-Trans-1-[2-[4-[5-fluoro-3-(4-fluorophenyl)-2,3-dihydro-1H-inden-1-yl]piperazin-1-yl]ethyl]-tetrahydro-2(1H)-pyrimidinethione,dihydrochloride; mp 205°–206° C., 26.7° (c0.5, water). Compd. (+)-30.

(–)-Trans-1-[2-[4-[5-fluoro-3-(4-fluorophenyl)-2,3-dihydro-1H-inden-1-yl]piperazin-1-yl]ethyl]-tetrahydro- 2(1H)-pyrimidinethione,dihydrochloride; mp 205°–206° C., [α]$_D$=–25.6° (c0.5, water). Compd. (–)-30.

The following compounds was prepared in a corresponding manner:

Trans-1-[2-[4-[5-chloro-3-(4-fluorophenyl)-2,3-dihydro-1H-inden-1-yl]piperazin-1-yl]ethyl]-2-imidazolidinthione,dimaleate; mp 183°–184° C. Compd. 31.

Trans-1-[2-[4-[5-chloro-3-(4-fluorophenyl)-2,3-dihydro-1H-inden-1-yl]piperazin-1-yl]ethyl]-tetrahydro-2(1H)-pyrimidinethione,dimaleate; mp.184°–185° C. Compd. 32.

(+)-Trans-1-[2-[4-[5-chloro-3-(4-fluorophenyl)-2,3-dihydro-1H-inden-1-yl]piperazin-1-yl]ethyl]-tetrahydro-2(1H)-pyrimidinethione,dihydrochloride; mp 212°–213° C., [α]D=+6.60 (c0.5, water). Compd. (+)-32.

(–)-Trans-1-[2-[4-[5-chloro-3-(4-fluorophenyl)-2,3-dihydro-1H-inden-1-yl]piperazin-1-yl]ethyl]-tetrahydro-2(1H)-pyrimidinethione,dihydrochloride; mp 212°–213° C., [α]$_D$=–6.6° (c0.5, water). Compd. (–)-32.

The following compounds were also prepared as described in Example 8, except that the diamines were treated with urea instead of carbondisulfide. A mixture of the diamine and urea in NMP was heated for 4 h at 140°–160° C., whereupon the reaction mixture was worked-up in a conventional manner.

(+)-Trans-1-[2-[4-[5-fluoro-3-(4-fluorophenyl)-2,3-dihydro-1H-inden-1-yl]piperazin-1-yl]ethyl]-tetrahydro-2(1H)-pyrimidinone,dimaleate; mp 170°–171° C., [α]$_D$= +16.0° (c0.5, water). Compd. (+)-33.

(–)-Trans-1-[2-[4-[5-fluoro-3-(4-fluorophenyl)-2,3-dihydro-1H-inden-1-yl]piperazin-1-yl]ethyl]-tetrahydro-2(1H)-pyrimidinone,dimaleate; mp 170°–171° C., [α]$_D$= –15.0° (c0.5, water). Compd. (–)-33.

(+)-Trans-1-[2-[4-[5-chloro-3-(4-fluorophenyl)-2,3-dihydro-1H-inden-1-yl]piperazin-1-yl]ethyl]-tetrahydro-2(1H)-pyrimidinone,dimaleate; mp 179°–180° C., [α]$_D$= +16.8° (c0.5, water). Compd. (+)-34.

(–)-Trans-1-[2-[4-[5-chloro-3-(4-fluorophenyl)-2,3-dihydro-1H-inden-1-yl]piperazin-1-yl]ethyl]-tetrahydro-2(1H)-pyrimidinone,dimaleate; mp 179°–180° C., [α]$_D$= –17.2° (c0.5, water). Compd. (–)-34.

(+)-Trans-1-[2-[4-[5-chloro-3-(4-fluorophenyl)-2,3-dihydro-1H-inden-1-yl]piperazin-1-yl]ethyl]-5,5-dimethyl-tetrahydro-2(1H)-pyrimidinone,dimaleate; mp 166°–168° C., Compd. 35.

EXAMPLE 9

Trans-1-[2-[4-[5-chloro-3-(4-fluorophenyl)-2,3-dihydro-1-H-inden-1-yl]piperazin-1-yl]ethyl]-3-isopropyl-2-imidazolidinthione, dimaleate (Compd. 36)

A mixture of 10 (15 g as the base), chloroacetonitrile (4.6 g) and potassium carbonate (10 g) in methyl ethylketone (400 ml) was refluxed overnight with stirring. After cooling and evaporation in vacuo the residue was treated with water and ether. The ether phase was dried and evaporated to give an oil which was chromatographed using 100 g of silica gel and ethyl acetate—methanol—triethylamine (80:10:10) as the mobile phase. Yield: 15 g, which was used without further purification.

The acetonitrile derivative (15 g) in dry tetrahydrofurane (150 ml) was treated under cooling with 3 g of pelleted lithium aluminium hydride. The reaction mixture was refluxed for 4 hours and worked-up in a conventional manner to give 15 g of the; crude N-(2-aminoethyl) derivative of 10.

Chloroacetylchloride (4.5 g) was added at 10°–15° C. to a stirred mixture of the aminoethyl derivative (15 g) and triethylamine (15 g) in trichloroethane. The mixture was stirred for 1 hour, whereupon isopropylamine (25 ml) was added. The reaction mixture was refluxed for 5 hours and was then treated with water. The organic phase was evaporated, and the resulting oil was dissolved in dry tetrahydrofurane (250 ml) and was then treated with 4 g of pelleted lithium aluminium hydride. After 2 hours' reflux the reaction mixture was worked-up in a conventional manner to give 11 g of crude trans-1 -[5-chloro-3-(4-fluorophenyl)-2,3-dihydro-1H-inden-1-yl]-4-[2-[(2-isopropylaminoethyl) amino]ethyl]piperazine, which was used without further purification in the final step:

Thiophosgene (2.8 g=1.9 ml) was added dropwise at 5° C. to a mixture of the crude product mentioned above (11 g) and triethylamine (2.8 g) in trichloroethane. The resulting mixture was stirred at room temperature for 15 min. and was then refluxed for 2 hours. After evaporation in vacuo the product was purified by extraction with 1N methanesulfonic acid followed by liberation of the base with 9N sodium hydroxide as described in Example 8. The resulting oil was purified by column chromatography using silica gel and acetone-toluene -isopropylamine—ammonium hydroxide (60:40:2:2) as a mobile phase. There was obtained 1.1 g of a base, which was transformed to the dimaleate salt. This salt was recrystallized twice from acetone/ether to give 0.4 g of 36, dimaleate, mp: 156°–159° C.

CHN calculated: 57.32%; 5.78%; 7.64%. CHN found: 57.33%; 5.76%; 7.17%.

EXAMPLE 10

Trans-1-[2-[4-[5-chloro-3-(4-fluorophenyl)-2,3-dihydro-1H-inden-1-yl]piperazin-1-yl]-ethyl]-3-(2-hydroxyethyl)-2-imidazolidinone, dimaleate, (Compd, 37)

Compound 4 (4,4 g as the base) was added to a suspension of potassium tertbutoxide (1.7 g) in dry toluene (200 ml). The mixture was kept at room temperature for 1 hour with stirring, whereupon ethylbromoacetate (2.5 g) was added. The; mixture was stirred for 1 hour at room temperature and was then poured into ice, The organic phase was separated, washed with water, dried and evaporated in vacuo. The resulting oil was dissolved in dry tetrahydrofurane (150 ml) whereupon lithium borohydride (1 g) was added. The mixture was stirred for 1 hour at room temperature and was then evaporated in vacuo. The residue was treated with ether and 1N methanesulfonic acid. The acid phase was basified with 9N sodium hydroxide and extracted with methylene chloride. After drying and evaporation in vacuo there was obtained 2.5 g of 37, which was converted to the maleate salt (in acetone). The salt was recrystallized from ethanol-methanol to give 1.4 pure 37, mp: 168°–170° C.

CHN calculated: 56.78%; 5.61%; 7.79%. CHN found: 56.45%; 5,62%; 7.83%

EXAMPLE 11

Trans-1-[2-[4-[5-chloro-3-(4-fluorophenyl-2,3-dihydro-1H-inden-1-yl]piperazin-1-yl]-ethyl]-2-pyrrolidinthione, dimaleate, (Compd. 38)

A mixture of Compound 15 (15 g) and Lawesson's reagent (5 g) in hexamethylphosphonic triamide (HMPA, 50 ml) was heated at 100° C. in a N$_2$-atmosphere for 1.5 hours. The reaction mixture was poured into water, treated with 9N sodium hydroxide (25 ml) and extracted with ether. The etherphase was extracted with 1N methane sulphonic acid, whereupon the base was liberated with 9N sodium hydroxide and again extracted with ether. The organic phase was evaporated to give 3.5 g of an oil, which was transformed to the dimaleate salt. This salt was recrystallized from ethanol (200 ml) to give 38, mp: 192°–1930° C.

CHN calculated: 57.42%; 5.41%; 6.09%. CHN found: 57.50%; 5.49%; 6.17%.

PHARMACOLOGICAL TESTS

The compounds of the invention were tested in well recognized and reliable methods. The tests were as follows, and the results are given in the following Table I. The well-known 5-$HT_2$ antagonists, ritanserin tefludazine and irindalone, and the corresponding analogues of Compounds 1, 9 and 4, respectively, substituted in the 6-position of the indane ring system in stead of the 5-position, i.e. compounds Nos. 39, 40 and 41, were included in the tests for comparison purposes. The results of the tests are shown in the Table 1.

INHIBITION OF $^3$H-KETANSERIN BINDING TO 5-$HT_2$ RECEPTORS IN RAT CORTEX IN VITRO

By this method the inhibition by drugs of the binding of $^3$H-Ketanserin (0,5 nM) to Serotonin $S_2$ (5-$HT_2$) receptors in membranes from rat is determined in vitro. Method in Hyttel, *Pharmacology & Toxicology*, 61, 126–129, 1987.
Procedure Male Wistar (Mol:Wist) rats (125–250 g) are sacrificed and cortical tissue is dissected and weighed. The tissue is homogenized (Ultra Turrax, 10 sec.) in 10 ml of ice-cold 50 mM tris buffer pH 7.7 (at 25° C.). The centrifuge glassware used in this step has been rinsed by sonication for 10 min. in ethanol. The homogenate is centrifuged twice at 20,000 g for 10 min. at 4° C. with rehomogenization of the pellet in 10 ml ice-cold buffer. The final pellet is homogenized in 500 vol (w/v) ice-cold buffer.

Incubation tubes kept on ice in triplicate receive 100 µl of drug solution in water (or water for total binding) and 2000 µl of tissue suspension (final tissue content corresponds to 4 mg original tissue). The binding experiment is initiated by addition of 100 µl of $^3$H-Ketanserin (final concentration 0.5 nM) and by placing the tubes in a 37° C. water bath. After incubation for 30 min. the samples are filtered under vacuum (0–50 mBar) through Whatman GF/F filters (25 mm). The tubes are rinsed with 5 ml ice-cold buffer which are then poured on the filters. Thereafter, the filters are washed with 2×5 ml of buffer. The filters are placed in counting vials and 4 ml of appropriate scintillation fluid (e.g. Picofluor™15) are added. After shaking for 1 h and storage 2 hrs in the dark the content of radioactivity is determined by liquid scintillation counting. Specific binding is obtained by subtracting the nonspecific binding in the presence of 1 µM mianserin.

For determination of the inhibition of binding five concentrations of drugs covering 3 decades are used.

The measured cpm are plotted against drug concentration on semilogarithmic paper and the best fitting S-shaped curve is drawn. The $IC_{50}$ value is determined as the concentration at which the binding is 50% of the total binding in control samples minus the nonspecific binding in the presence of 1 µM mianserin.

$^3$H-Ketanserin=[ethylene-$^3$H]-Ketanserin hydrochloride from New England Nuclear, specific activity 60–80 Ci/mmol).

INHIBITION OF $^3$H-SPIPERONE BINDING TO DOPAMINE D-2 RECEPTORS IN RAT CORPUS STRIATUM IN VITRO

By this method the inhibition by drugs of the binding of $^3$H-spiperone (0.5 nM) to dopamine D-2 receptors in membranes from rat corpus striatum is determined in vitro. Method and results in Hyttel & Larsen, *J. Neurochem*, 44, 1615–1622, 1985).
Procedure Male Wistar (Mol:Wistar) rats (125–250 g) are sacrificed and striatal tissue is dissected and weighed. The tissue is homogenized (Ultra Turrax, 10 sec.) in 10 ml of ice-cold 50 mM K-phosphate buffer pH 7.4 (at 25° C.). The homogenate is centrifuged twice at 20,000 g for 10 min. at 4° C. with rehomogenization of the pellet in 10 ml ice-cold buffer. The final pellet is homogenized in 1300 vol (w/v) ice-cold buffer.

Incubation tubes kept on ice in triplicate receive 100 µl of drug solution in water (or water for total binding) and 4000 µl of tissue suspension (final tissue content corresponds to 3.08 mg original tissue). The binding experimental is initiated by addition of 100 µl of $^3$H-spiperone (final concentration 0.5 nM) and by placing the tubes in a 37° C. water bath. After incubation for 10 min. the samples are filtered under vacuum (0–50 mBar) through Whatman GF/F filters (25 mm). The tubes are rinsed with 5 ml ice-cold buffer which are then poured on the filters. Thereafter, the filters are washed with 2×5 ml of buffer. The filters are placed in counting vials and 4 ml of appropriate scintillation fluid (e.g. Picofluor ™15) are added. After shaking for 1 h and storage 2 hrs in the dark the content of radioactivity is determined by liquid scintillation counting. Specific binding is obtained by subtracting the nonspecific binding in the presence of 10 µM of 6,7-ADTN.

For determination of the inhibition of binding five concentrations of drugs covering 3 decades are used.

The measured cpm are plotted against drug concentration on semilogarithmic paper and the best fitting S-shaped curve is drawn. The $IC_{50}$ value is determined as the concentration at which the binding is 50% of the total binding in control samples minus the nonspecific binding in the presence of 10 µM of 6,7-ADTN.

$^3$H-Spiperone=[phenyl-4-$^3$H]-spiperone from Amersham International plc. England, specific activity 15–25 Ci/mmol.

INHIBITION OF $^3$H-PRAZOSIN BINDING TO $\alpha_1$ ADRENOCEPTORS IN RAT BRAIN IN VITRO By this method the inhibition of the binding of $^3$H-Prazosin (0.25 nM) to $\alpha_1$ adrenoceptors in membranes from rat brain is determined in vitro. Method and results in Hyttel & Larsen, *J. Neurochem*, 44, 1615–1622, 1985; Skarsfeldt & Hyttel, *Eur. J. Pharmacol.* 125, 323–340, 1986.
Procedure Male Wistar (Mol:Wist) rats (125–200 g) are sacrificed and brain tissue is dissected and weighed. The tissue is homogenized (Ultra Turrax, 10 sec.) in 10 ml of ice-cold 50 nM Tris buffer pH 7,7 (at 25° C.). The homogenate is centrifuged twice at 20,000 g for 10 min. at 4° C. with rehomogenization of the pellet in 10 ml ice-cold buffer. The final pellet is homogenized in 400 vol (w/v) ice-cold buffer.

Incubation tubes kept on ice in triplicate receive 100 µl of drug solution in water (or water for total binding) and 4000µl of tissue suspension (final tissue content corresponds to 10 mg original tissue). The binding experiment is initiated by addition of 100 µl of $^3$H-Prazosin (final concentration 0.25 nM) and by placing the tubes in a 25° C. water bath. After incubation for 20 min. the samples are filtered under vacuum (0–50 mBar) through Whatman GF/F filters (25 mm). The tubes are rinsed with 5 ml ice-cold buffer which then are poured on the filters. Thereafter, the filters are washed with 5 ml of buffer. The filters are placed in counting vials and 4 ml of appropriate scintillation fluid (e.g. Picofluor™15) are added. After shaking for 1 h and storage 2 hrs in the dark the content of radioactivity is determined by liquid scintillation counting. Specific binding is obtained by subtracting the nonspecific binding in the presence of 1 µM of Prazosin.

For determination of the inhibition of binding five concentrations of drugs covering 3 decades are used.

The measured cpm are plotted against drug concentration on semilogarithmic paper and the best fitting S-shaped curve is drawn. The $IC_{50}$ value is determined as the concentration at which the binding is 50% of the total binding in control samples minus the nonspecific binding in the presence of 1 µM of Prazosin.

$^3$H-Prazosin=[furoyl-5-$^3$H]-Prazosin from New England Nuclear, specific activity approximately 20 Ci/mmol.

TABLE 1

| | Receptor Binding; $IC_{50}$(nM) | | |
|---|---|---|---|
| Compound No. | 5-HT$_2$ $^3$H-Ket | DA D-2 $^3$H-Spi | α$_1$ $^3$H-Praz |
| 1 | 2.9 | 760 | 320 |
| (+)-1 | 2.0 | 290 | 330 |
| 2 | 21 | 1100 | 150 |
| (+)-2 | 12 | 330 | 72 |
| (−)-2 | 500 | 22000 | 1100 |
| 3 | 25 | 2200 | 230 |
| (−)-3 | 11 | 370 | 210 |
| (+)-3 | 230 | 6300 | 2500 |
| 4 | 2.9 | 360 | 200 |
| 5 | 8.9 | 1300 | 380 |
| 6 | 56 | 2600 | 1000 |
| 7 | 7.9 | 2800 | 240 |
| 8 | 12 | 1000 | 270 |
| 9 | 3.7 | 370 | 220 |
| 10 | 11 | 2500 | 840 |
| (−)-10 | 15 | 730 | 390 |
| (+)-10 | 3300 | 28000 | |
| 11 | 3.9 | 280 | 260 |
| (+)-11 | 75 | 1300 | 340 |
| (−)-11 | 1.1 | 200 | 210 |
| 12 | 3.0 | 450 | 120 |
| 13 | 3.7 | 510 | 350 |
| 14 | 23 | 550 | 140 |
| 15 | 10 | 500 | 370 |
| 16 | 10 | 160 | 73 |
| 17 | 44 | 300 | 310 |
| 18 | 2.8 | 190 | 600 |
| 19 | 2.6 | 260 | 240 |
| 20 | 9.9 | 750 | 510 |
| 21 | 3.5 | 920 | 670 |
| 22 | 3.5 | 1100 | 240 |
| 23 | 4.0 | 720 | 250 |
| 24 | 6.4 | 240 | 270 |
| 25 | 5.6 | 110 | 66 |
| 26 | 11 | 450 | 60 |
| 27 | 15 | 280 | 180 |
| 28 | 26 | 490 | 970 |
| 29 | 1.5 | 230 | 110 |
| 30 | 1.7 | 220 | 110 |
| (+)-30 | 0.95 | 140 | 43 |
| (−)-30 | 42 | 2900 | |
| 31 | 1.5 | 67 | 52 |
| 32 | 1.5 | 93 | 170 |
| (+)-32 | 21 | 490 | 350 |
| (−)-32 | 0.75 | 33 | 67 |
| (+)-33 | 1.1 | 280 | 41 |
| (−)-33 | 57 | 4600 | |
| (+)-34 | 120 | 1700 | |
| (−)-34 | 1.3 | 94 | 62 |
| 35 | 4.8 | 150 | 120 |
| 36 | 3.6 | 260 | 69 |
| 37 | 6.1 | 320 | 710 |
| 38 | 5.3 | 290 | 260 |
| Tefludazine | 4.6 | 10 | 17 |
| Irindalon | 3.4 | 400 | 16 |
| Ritanserin | 0.40 | 12 | 47 |
| 39 | | 21 | 8.3 |

TABLE 1-continued

| | Receptor Binding; $IC_{50}$(nM) | | |
|---|---|---|---|
| Compound No. | 5-HT$_2$ $^3$H-Ket | DA D-2 $^3$H-Spi | α$_1$ $^3$H-Praz |
| 40 | 0.71 | 43 | 12 |
| 41 | | 17 | 3.1 |

QUIPAZINE INHIBITION

Quipazine is a 5-HT$_2$ agonist, which induces head twitches in rats. The test is an in vivo test for 5-HT$_2$-antagonistic effect testing the ability to inhibit head twitches. The method and test results for some reference substances are published by Arnt et al. (*Drug Development Research*, 16, 59–70, 1989).

In this test the compounds showed effects with $ED_{50}$ values down to 0.01 mg/kg.

LIGHT/DARK DISCRIMATION TEST IN MICE

This test was carried out in accordance with the method described in Costall et al. *Br. J. Pharmacol.* 90 275P (1987).

The test was conducted using a two compartment activity box in which the actions of anxiolytic compounds to reduce aversion against a brightly-lit environment may be readily detected. The box is designed as an open-top experimental box (45*27*27 cm) one third of which was partitioned from the rest, painted black and illuminated with red light. The remainder of the box was painted white and brightly illuminated (1000 W). The floor of each area was lined into squares. Behavioral changes were determined for each area from video recordings for periods of 40 min.

Data obtained from dose groups of 5 animals (male albino BKW mice, 25–30 g) were analysed using single factor analysis of variance, and Dunnett's t-test. Test compounds were given intraperitoneally 45 min before testing. In this test model Compounds (+)-30, (−)-32 and (+)-33 showed significant anxiolytic activity ($p<0.05$) in doses from 0.01 to 1 mg/kg.

LIGHT/DARK DISCRIMINATION TEST IN RATS

The test was carried out similarly to the test in mice described above, however modified in accordance with F. C. Colpaert et al., Psychopharmacology (1985) 86:45–54. The test used Wistar WU rats. In this test model Compounds (−)-32 and (+)-33 showed significant anxiolytic activity ($p<0.05$) in doses from 0.1 to 1 mg/kg.

All the compounds except the weak or inactive stereoisomers of Compd. 2, 3, 10, 11, 30, 32, 33, and 34 show high affinity to 5-HT$_2$ receptors and have much lower affinity to D-2 receptors and α$_1$ adrenoceptors than the prior art compounds included in the tests for comparison purposes. Tefludazine, a 6-substituted 1-piperazino-3-phenylindan derivative representative for U. S. Pat. No. 4,443,448, shows high affinity to all three receptor types whereas irindalone, a 1-piperazino-3-(fluorophenyl)indan derivative representative for U.S. Pat. No. 4,684,650, in addition to a high affinity to 5-HT$_2$ receptors has a significant affinity to oh adrenoceptors. The dramatic effect of the change from 6- to 5-substitution is illustrated by comparison of the receptor profiles of the 6-substituted derivatives 39, 40 and 41 with their otherwise identical 5-substituted analoques 1, 9 and 4.

FORMULATION EXAMPLES

The pharmaceutical formulations of the invention may be prepared by conventional methods in the art. For example: Tablets may be prepared by mixing the active ingredient with ordinary adjuvants and/or diluents and subsequently compressing the mixture in a conventional tabletting machine. Examples of adjuvants or diluents comprise: corn starch, potato starch, talcum, magnesium stearate, gelatine, lactose, gums, and the like. Any other adjuvants or additives usually used for such purposes such as colourings, flavourings, preservatives etc. may be used provided that they are compatible with the active ingredients. Solutions for injections may be prepared by dissolving the active ingredient and possible additives in a part of the solvent for injection, preferably sterile water, adjusting the solution to desired volume, sterilization of the solution and filling in suitable ampules or vials. Any suitable additive conventionally used in the art may be added, such as tonicity agents, preservatives, antioxidants, etc.

Typical examples of recipes for the formulation of the invention are as follows:

1) Tablets containing 5 milligrams of Compound 4c calculated as the free base:

| | |
|---|---|
| Comp. (+)–33 | 5 mg |
| Lactose | 18 mg |
| Potato starch | 27 mg |
| Sucrose | 58 mg |
| Sorbitol | 3 mg |
| Talcum | 5 mg |
| Gelatine | 2 mg |
| Povidone | 1 mg |
| Magnesium stearate | 0.5 mg |

2) Tablets containing 50 milligrams of Compound 4b calculated as the free base:

| | |
|---|---|
| Comp. (+)–30 | 50 mg |
| Lactose | 16 mg |
| Potato starch | 45 mg |
| Sucrose | 106 mg |
| Sorbitol | 6 mg |
| Talcum | 9 mg |
| Gelatine | 4 mg |
| Povidone | 3 mg |
| Magnesium stearate | 0.6 mg |

3) Syrup containing per milliliter:

| | |
|---|---|
| Comp. (–)–32 | 10 mg |
| Sorbitol | 500 mg |
| Tragacanth | 7 mg |
| Glycerol | 50 mg |
| Methyl-paraben | 1 mg |
| Propyl-paraben | 0.1 mg |
| Ethanol | 0.005 ml |
| Water | ad 1 ml |

4) Solution for injection containing per milliliter:

| | |
|---|---|
| Comp. (–)–34 | 50 mg |
| Acetic acid | 17.9 mg |
| Sterile water | ad 1 ml |

5) Solution for injection containing per milliliter:

| | |
|---|---|
| Comp. (–)–11 | 10 mg |
| Sorbitol | 42.9 mg |
| Acetic acid | 0.63 mg |
| Sodium hydroxide | 22 mg |
| Sterile water | ad 1 ml |

We claim:

1. A 5- substituted trans-1-piperazinolndan compound having the formula:

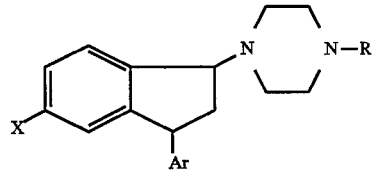

wherein X is chlorine, fluorine, methyl, or trifluoromethyl;
R is a substituent having the formula;

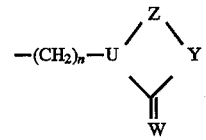

wherein n is 2;
Y is O, $CH_2$, or N-$R^1$, $R^1$ being hydrogen, isopropyl, or phenyl;
W is O or S;
Z is —$GH_2CH_2$—, —$CH_2$—$CH_2$—$CH_2$—, or 1,2-phenylene; and Ar is 4-fluorophenyl;
or a pharmaceutically acceptable acid addition salt thereof.

2. A 5-substituted trans-1-piparazinoindan derivative according to claim 1, wherein R is a group of the formula;

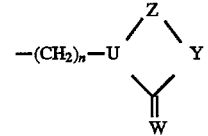

wherein n is 2; W is O or S; Z is —$CH_2CH_2$— or —$CH_2$—$CH_2$—$CH_2$—; and Y is N-$R^1$.

3. A substituted trans-1-piperazinoindan derivative according to claim 1, wherein X is Cl or F.

4. A 5-substituted trans-1-piperazinoindan, compound selected from the group consisting of:
(–)-Trans-1-[2-[4-[5-chloro-3-(4-fluorophenyl)-2,3-dihydro-1H-inden-1-yl]piperazin-1-yl]-ethyl]-3-isopropyl-2-imidazolidinone;
(+)-Trans-1-[2-[4-[5-fluoro-3-(4-fluorophenyl)-2,3-dihydro-1H-inden-1-yl]piperazin-1-yl]ethyl]-tetrahydro-2(1H)-pyrimidinethione;
(–)-Trans-1-[2-[4-[5-chloro-3-(4-fluorophenyl)-2,3-dihydro-1H-inden-1-yl]piperazin-1-yl]-ethyl]-tetrahydro-2(1H)-pyrimidinethione;
(+)-Trans-1-[2-[4-[5-fluoro-3-(4-fluorophenyl)-2,3-dihydro-1H-inden-1-yl]piperazin-1-yl]ethyl]-tetrahydro-2(1H)-pyrimidinone; and
(–)-Trans-1-[2-[4-[5-chloro-3-(4-fluorophenyl)-2,3-dihydro-1H-inden-1-yl]piperazine-1-yl]ethyl]-tetrahydro-2(1H)-pyrimidinone;

and acid addition salts thereof.

5. A 5-substituted trans-1-piperazinoindan derivative according to claim 4, wherein said derivative is selected from the group consisting of:

(−)-Trans-1-[2-[4-[5-chloro-3-(4-fluorophenyl)-2,3-dihydro-1H-inden-1-yl]piperazin-1-yl]-ethyl]-3-isopropyl-2-imidazolidinone, dimaleate;

(+)-Trans-1-[2-[4-[5-fluoro-3-(4-fluorophenyl)-2,3-dihydro-1H-inden-1-yl]piperazin-1-yl]ethyl]-tetrahydro-2(1H)-pyrimidinethione, dihydrochloride;

(−)-Trans-1-[2-[4-[5-chloro-3-(4-fluorophenyl)-2,3-dihydro-1H-inden-1-yl]piperazin-1-yl]-ethyl]-tetrahydro-2(1H)-pyrimidinethione, dihydrochloride;

(+)-Trans-1-[2-[4-[5-fluoro-3-(4-fluorophenyl)-2,3-dihydro-1H-inden-1-yl]piperazin-1-yl]ethyl]-tetrahydro-2(1H)-pyrimidinone, dimaleate; and (−)-Trans-1-[2-[4-[5-chloro-3-(4-fluorophenyl)-2,3-dihydro-1H-inden-1-yl]piperazin-1-yl]ethyl]-tetrahydro-2(1H)-pyrimidinone, dimaleate.

6. A pharmaceutical preparation comprising at least one compound according to claim 1 together with a pharmaceutically acceptable carrier or diluent.

* * * * *

UNITED STATES PATENT AND TRADEMARK OFFICE
CERTIFICATE OF CORRECTION

PATENT NO.    : 5,643,784
DATED         : July 1, 1997
INVENTOR(S)   : Klaus P. Bøgesø and Peter Bregnedal It is certified that error appears in the above-identified patent and that said Letters Patent is hereby corrected as shown below:

Column 20,
Line 25, delete " 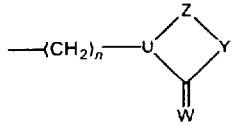

"

and replace with -- 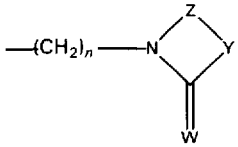

Line 35, delete "-GH$_2$-CH$_2$-" and replace with -- -CH$_2$-CH$_2$- --.

Signed and Sealed this

Twenty-sixth Day of March, 2002

Attest:

JAMES E. ROGAN
Attesting Officer    Director of the United States Patent and Trademark Office